United States Patent [19]

Tuohig et al.

[11] Patent Number: 4,469,626
[45] Date of Patent: Sep. 4, 1984

[54] COMPOSITION AND METHOD FOR FORMING A THICK FILM OXYGEN SENSING ELEMENT

[75] Inventors: Wayne D. Tuohig, Birmingham; Calman S. Sagady, West Bloomfield, both of Mich.

[73] Assignee: The Bendix Corporation, Southfield, Mich.

[21] Appl. No.: 265,748

[22] Filed: May 21, 1981

Related U.S. Application Data

[62] Division of Ser. No. 150,105, May 15, 1980, abandoned.

[51] Int. Cl.$^3$ .............................................. A01B 1/06
[52] U.S. Cl. .................................. 252/514; 252/520; 338/34; 106/1.15; 106/1.21
[58] Field of Search ............... 252/514, 520, 518, 408, 252/472, 466 PT; 338/34, 35, 308; 106/1.15, 1.21, 311; 23/232 E, 254 E; 73/27 R, 23

[56] References Cited

U.S. PATENT DOCUMENTS 4,000,089 12/1976 Senda .................................. 252/514
4,066,413 1/1978 Segawa et al. ..................... 23/254 E

*Primary Examiner*—Josephine Barr
*Attorney, Agent, or Firm*—Leo H. McCormick, Jr.; Ken C. Decker

[57] ABSTRACT

A composition for forming a resistive type oxygen sensing element and a method for forming such elements, wherein a mixture of titanium dioxide, glass frit and platinum are used, the titanium dioxide having a particle size within a specific range, and a particular ratio to the other two components of the mixture. The composition is screened over printed platinum leads on a ceramic substrate, with a resistor material also used as a thermistor, and the resistive materials having their own conductive leads in addition to a common lead to the terminals of an oxygen sensor.

4 Claims, 8 Drawing Figures

COMPOSITION AND METHOD FOR FORMING A THICK FILM OXYGEN SENSING ELEMENT

This is a division of application Ser. No. 150,105 filed May 15, 1980, now abandoned.

BACKGROUND OF THE INVENTION

The present invention relates to a composition for use in forming a thick film resistive type oxygen sensing element and a method of forming thick film oxygen sensors adapted for use in automotive exhaust systems.

Resistive type oxygen sensors are based on the ability of certain oxides, such as titanium dioxide, to exchange oxygen with the surrounding environment. As oxygen is gained or lost from the oxide, the resistivity, and conversely the conductivity of the oxide is altered, and measurement of the resistivity can be used as a means for measuring the oxygen content of an exhaust gas within which the sensing element is situated. Examples of such sensing elements are given in U.S. Pat. No. 4,066,413 and U.S. Pat. No. 4,007,435, as well as discussions of the function of the resistive type sensor material and problems associated with measurement of the oxygen content of automotive exhaust. Discrete types of titanium dioxide resistive sensors have also been disclosed, for example in U.S. Pat. No. 4,147,513, assigned to the assignee of the present invention, the contents of which are incorporated herein, but the use of platinum wire leads renders the discrete sensor expensive and difficult to manufacture, as well as subject to mechanical damage.

By use of the present invention, resistive type oxygen sensors are formed which are structurally sound, readily manufactured, and relatively inexpensive.

SUMMARY OF THE INVENTION

The invention provides a composition for forming a resistive oxygen sensitive layer on an insulating ceramic substrate and a method for forming an oxygen sensing element. The layer forms a thick film oxygen sensing element that is ideal for use in an air-to-fuel ratio sensor such as is used in an automobile exhaust system. The composition is characterized by a mixture of rutile titanium dioxide, a fluxing agent and platinum combined with a vehicle such as Venice turpentine. Titanium dioxide comprises about 28 to 58 percent of the weight of the mixture and has a mean particle size of below 10 micrometers, the fluxing agent about 2 to 12 percent by weight and the platinum about 40 to 60 percent by weight. The thick film layer of the disclosed composition on a ceramic substrate has a thickness of between 10 and 30 micrometers after it is screened to cover a portion of a pair of electrodes and then fired. Upon firing of the composition, a layer is formed which comprises a continuous sintered network of titanium dioxide particles containing isolated particles of platinum.

DESCRIPTION OF THE INVENTION

Figure 1:
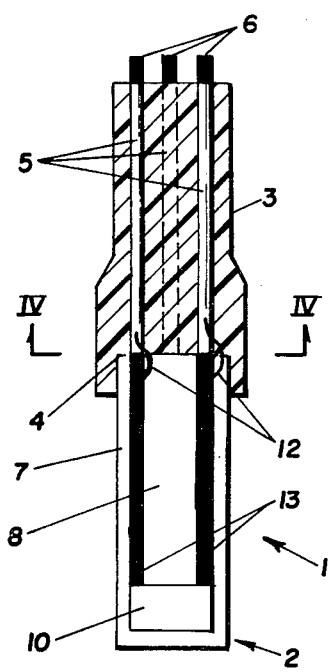
FIG. 1 is a schematic view of an oxygen sensor having a thick film layer applied according to the present invention.
Figure 2:
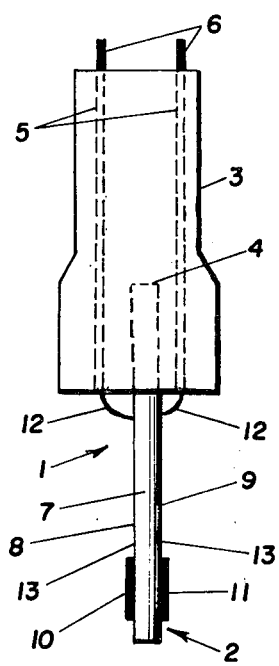
FIG. 2 is a schematic side view of the oxygen sensor illustrated in FIG. 1.

Referring now to both FIGS. 1 and 2, an oxygen sensor, generally indicated by the numeral 1, is formed incorporating the composition of the present invention. The oxygen sensor 1 includes a sensing element 2 and a supporting insulating ceramic mount 3 which has a recess 4 in the lower portion thereof for receiving the sensing element 2. The ceramic mount 3 also has a plurality of passages 5 therethrough, in which the terminals 6 are mounted. The sensor element 2 includes a ceramic substrate 7 having a front surface 8 and a back surface 9 which support a first resistor 10, the resistance of which varies only as a function of temperature, and a second resistor 11 comprised of the titania composition of the instant invention, respectively. The resistors are in an electrically conductive relationship by means of a plurality of gold fly leads 12 and electrically conductive patterns generally indicated by the numeral 13.

Figure 3A:
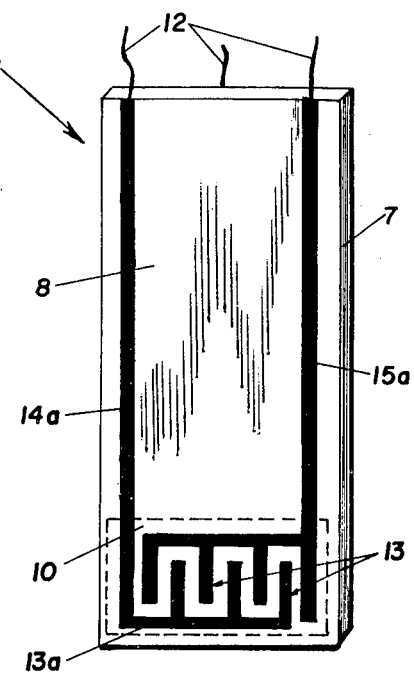
FIG. 3a is an isometric view of the front surface of the sensing element of the oxygen sensor.
Figure 3B:
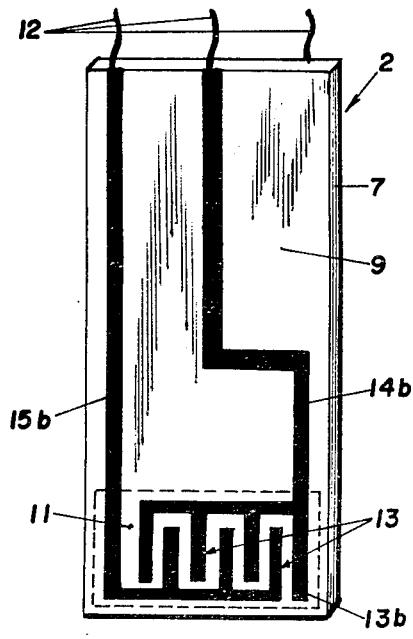
FIG. 3b is an isometric view of the back surface of the sensing element of the oxygen sensor.

In the preferred embodiment of the sensor element 2, the front side of which is seen in FIG. 3a and the back side of FIG. 3b, a conductive pattern of platinum 13 is applied to the substrate 7 so that a first section 13a which includes a conductive lead 14a extending therefrom is formed on the front side 8 of the substrate and a distinct second section 13b which includes a conductive lead 14b is formed on the back surface thereof. A thermistor 10 is superimposed on the first section 13a of the pattern and a thick film layer of titanium dioxide 11 is superimposed on the back section 13b of the platinum pattern. A first common conductive lead 15a of electrically conductive material, such as platinum, is applied to the substrate 7 so as to be in electrical contact with the thermistor 10. A second lead 15b of similar electrically conductive material is applied on the substrate so as to be in electrical contact with the titania resistor 11. The leads 15a and 15b may be commonly connected in an electrically conductive relation by means of the fly leads 12. Preferably, a fly lead formed of thin gold wire is attached to each of the leads 14a, 14b, 15a and 15b, in order to electrically connect said leads with the terminals 6, after passing through the passages 5. In order to connect the leads 15a and 15b, as mentioned, it is only necessary to join the particular two fly leads attached thereto for union with a single terminal 6. Each of the remaining fly leads 12 enter into one of the remaining passages 5 for union with a terminal 6.

Figure 4:
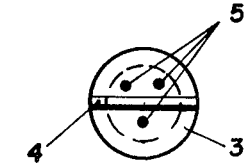
FIG. 4 is a bottom plan view of the oxygen sensor along lines IV—IV of FIG. 1.

Turning briefly to FIG. 4, it will be noted that the recess 4 is positioned between triangularly configured passages 5 in order to facilitate the union of the fly leads with the terminals.

Figure 5:
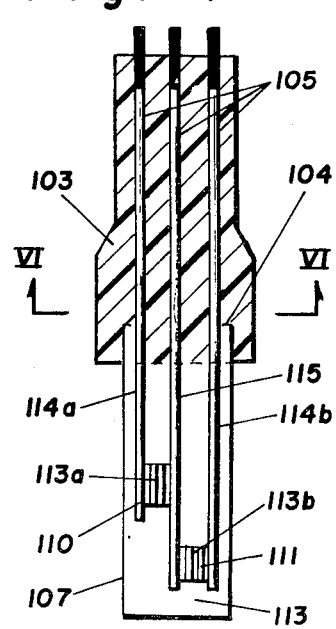
FIG. 5 is a schematic view of an alternative embodiment of an oxygen sensor incorporating the thick film layer applied according to the present invention.
Figure 6:
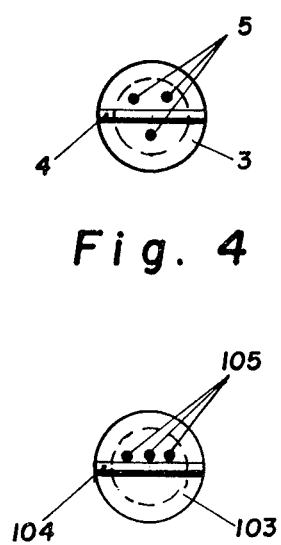
FIG. 6 is a bottom plan view of the alternate embodiment of the oxygen sensor along lines VI—VI of FIG. 5.

In an alternate embodiment, illustrated in FIG. 5, both resistive layers 110 and 111 are applied to one side of the substrate 107. The conductive pattern of platinum is applied which includes a first section 113a with a lead 114a and a second distinct section 113b with a lead 114b extending therefrom. A thermistor 110 is superimposed over the first section and a titania resistor 111 is superimposed onto the second section. At least one lead of conductive material 115 is applied to the substrate in order to provide a common path of electrical conductivity between resistors 110 and 111. As can be seen in FIG. 6, when the sensing material is applied to only one side of the substrate it is convenient to align the passages 105 along one side of the recess 104 in the ceramic mount 103.

The titanium oxide resistive oxygen sensitive layer 11 is formed as a thick film composition and applied by the process of the present invention. The titanium dioxide layer is formed by printing or screening onto the ceramic substrate over the platinum leads and is in contact with one of the distinct sections of the platinum pattern and a common conductive lead. The layer is applied at a thickness of between about 10 to 30 micrometers.

The composition for forming the resistive oxygen sensitive layer on the insulating ceramic substrate is composed of a mixture of titanium dioxide (rutile) of a particular size, a fluxing agent and platinum. The titanium dioxide of this composition has a mean particle size of less than about 10 micrometers. The amount of titanium in the mixture is within the range of about 28 to 58 percent by weight of the total weight of the mixture. The preferred weight is about 40 percent of the mixture's weight.

A second component of the composition is a fluxing agent such as glass frit or a multivalent oxide which improves the bonding between the titanium, platinum and substrate. The fluxing agent should be present within the mixture in an amount within the range of about 2 to 12 percent by weight of the total weight of the mixture.

The third component of the composition of the present invention comprises a platinum paste such as those commercially available for use in forming platinum conductors. Such pastes are sold under the names of Engelhard A3786 and Engelhard 6082. The platinum composes by weight between about 40 to 80 percent of the total weight of the composition.

In order to effect screening or printing of the composition on the substrate, the composition is thinned to a consistency suitable for such application by the addition thereto of an organic liquid carrier. The carrier should be one that will be completely vaporized during the initial stage of firing of the sensor element, and can comprise turpentine or other known carriers for solid inorganic powdery materials. Such carriers should be completely vaporized below a temperature of about 850° C. which is used in the firing step of the formation of the sensor. Examples of such carriers are alpha terpineol and Venice turpentine. A layer of sensing material is formed which comprises a continuous sintered network of titanium oxide particles containing isolated particles of platinum.

After formation of the conductive pattern 113 and conductive lead 115 in the single sided embodiment, or pattern 13 and leads 15a and 15b in the preferred embodiment on the sensor 2, the sensor is subjected to a firing step where it is heated to a temperature of 850° C. with a soaking period at that temperature used to assure firing of the same.

A screening is then effected to cover a portion of one distinct section of the pattern and a portion of the lead. The screening is done using a thermistor material comprising zirconium dioxide as a major constituent in admixture with a fluxing agent, and a small amount of platinum combined with a vehicle such as Venice turpentine. The sensor is then fired at about 1250° C.

A second screening is then effected, covering a portion of a second distinct section of the pattern and a portion of the lead, the second screening done using the composition of the present invention. The sensing element 2 is then subjected to a firing step where the sensing element is heated in air to a temperature of 850° C. with a soaking period at that temperature used to assure firing of the same.

Figure 7:
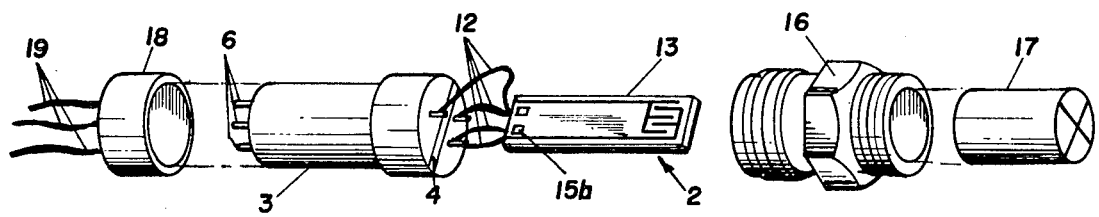
FIG. 7 is an exploded isometric view of the oxygen sensor of the present invention as the same would be assembled for use in an automobile engine's exhaust system.

The sensing element 2 is then mated within the recess 4 of the ceramic mount 3 and the mated sensor mounted within a shell 16 as illustrated in FIG. 7. Electrical conductive contact is established between terminals 6 and the screened conductive elements on the substrate by means of a plurality of gold fly leads 12. In the preferred embodiment in which a resistive layer is screened on each side of the substrate, two of the fly leads 12 bring the leads 15a and 15b into an electrically conductive relationship in a common passage 5.

The shell 16 which may be a modified spark plug shell or the like has a vented shield 17 extending from its forward tip. The vented shield 17 is provided with air flow through means to allow sensor contact with the surrounding environment. The shell 16 is retained by crimping it upper portion against the mount 3. A talc gasket may also be provided. The boot 18 which fits over the mount 3 has leads 19 for electrically connecting the terminals 6 of the oxygen sensing device to a control unit for control of the air/fuel ratio fed to the automotive engine in response to the oxygen sensor signals.

A composition and method for forming a resistive oxygen sensitive layer on an insulating ceramic substrate, ideal for use in an air-to-fuel ratio sensor, has been described.

What is claimed is:

1. A composition for forming a resistive oxygen sensitive layer as a conductive pattern on an insulative ceramic substrate to produce a thick film oxygen sensor element comprising:

a mixture of rutile titanium dioxide, a fluxing agent and platinum, wherein said titanium dioxide is present in an amount of 28–58 percent by weight of the mixture and has a mean particle size of below 10 micrometers, said fluxing agent is present in an amount of between 2–12 percent by weight of the mixture, and said platinum is present in an amount of between 40–80 percent by weight of the mixture such that upon firing of the composition, a layer of between 10–30 micrometers is formed which comprises a continuous sintered network of titanium oxide particles surrounded by isolated platinum particles.

2. A composition for forming a resistive oxygen sensitive layer as defined in claim 1 wherein said titanium dioxide is present in an amount of 40 percent by weight of the mixture.

3. A composition for forming a resistive oxygen sensitive layer as defined in claim 1 wherein said composition is disposed in an organic liquid carrier to enable screening of the composition on a ceramic substrate, said organic liquid carrier being completely vaporizable at a temperature below about 850° C.

4. A composition for forming a resistive oxygen sensitive layer as defined in claim 4 wherein said organic liquid carrier is alpha terpineol.

* * * * *